United States Patent [19]

David et al.

[11] 4,335,097

[45] Jun. 15, 1982

[54] STABILIZED, PROSTAGLANDIN-CONTAINING TABLETS WITH CONTROLLED RATE OF SOLUBILITY, FOR LOCAL USE AND PROCESS FOR THE PREPARATION THEREOF

[75] Inventors: Agoston David; Tibor Horvath; Csaba Kiss; Gábor Nagy; Kálmán Simon; Ilona Simonidesz nee Vermes; Agnes Udvardi; Sándor Virág, all of Budapest, Hungary

[73] Assignee: Chinoin Gyógyszer és Vegyészeti Termékek Gyára Rt., Budapest, Hungary

[21] Appl. No.: 225,361

[22] Filed: Jan. 15, 1981

[51] Int. Cl.³ .................... A61K 9/00; A61K 31/215; A61K 31/19
[52] U.S. Cl. ........................ 424/14; 424/19; 424/305; 424/317
[58] Field of Search ............. 424/19, 14, 305, 317

[56] References Cited

U.S. PATENT DOCUMENTS 3,937,801 2/1976 Lippmann ................ 424/317

OTHER PUBLICATIONS

Lippert—Chem. Abst. vol. 82, (1975) p. 610s.

*Primary Examiner*—Sam Rosen
*Attorney, Agent, or Firm*—Karl F. Ross

[57] ABSTRACT

The invention relates to stabilized, prostaglandin-containing tablets with controlled rate of solubility, for local use and a process for the preparation thereof. The tablets according to the invention comprise 0.2 to 20% by weight of one or more natural or synthetic prostaglandins, 0.4 to 40% by weight of a non-toxic buffer, which adjusts the pH of the liquid film formed on the surface of the solid phase due to air humidity, to 3 to 5, 1 to 50% by weight of stearic acid, 0 to 15% by weight of an alkali earth metal stearate, 10 to 95% by weight of lactose and/or mannite, 0 to 15% by weight of a further granulation aid, 1 to 30% by weight of a disintegrating agent and optionally 0.5 to 10% by weight of a flavoring and aroma substance and are prepared under a pressure of 500 to 2000 kp./cm². (49.03 to 196.13 MPa).

9 Claims, No Drawings

STABILIZED, PROSTAGLANDIN-CONTAINING TABLETS WITH CONTROLLED RATE OF SOLUBILITY, FOR LOCAL USE AND PROCESS FOR THE PREPARATION THEREOF

FIELD OF THE INVENTION

This invention relates to stabilized, prostaglandin-containing tablets with a controlled rate of solubility, for local use, and a process for their preparation.

BACKGROUND OF THE INVENTION

The clinical use of prostaglandin derivatives, primarily for gynecological purposes was made possible by the experiments of N. Winquist et al. [Lancet, 889, 1970], and since that time considerable research activity has been going on in this field all over the world including Hungary [Orvosi Hetilap 113, 919–927 (1972); Magyar Nöorvosok Lapja 37, 97–103 (1974)]. Prostaglandin $F_{2\alpha}$ is generally administered as an injectable solution, for example for interruption of pregnancy, dilation of os uteri and inducing labor. An injectable solution suitable for these purposes is for example disclosed in the Hungarian Patent Specification No. 171,997.

Since the intra-uteral, intraamnial or intravenous administration of the injectable preparations has to be carried out with extra care and skilfulness, there is a long standing demand for other formulations, which can be handled and administered in a more simple way.

It is also known that the oral preparations provide the desired effect only in considerably high doses, and their administration is generally accompanied by an unreasonably large number of side effects.

In gynecology vaginal tablets and semisolid formulations have been used for a long time for local administration. Due to physiological and anatomical reasons, however, such prostaglandin preparations can only restrictedly be used in gynecology and considerable overdoses are required to obtain the desired therapeutic effect. In addition, the use of such preparations is accompanied by numerous uncertainties.

It thus is desirable to prepare and administer cervical or sublingual tablets, from which the active ingredient is liberated at a constant rate, at the locus of treatment. By the processes known in the art prostaglandins could, however, not be formulated into such tablets, primarily because of their well-known instability. The cervical or sublingual tablets, prepared by conventional techniques rapidly lose their active ingredient content during storage, as is shown in Table 1. The tablet tested contained 2.5 mg. of $PGF_{2\alpha}$, 24.5 mg. of lactose and 1 mg. of stearin.

TABLE 1

| Storage temperature [°C.] | 0 | 30 | 40 | 50 | 60 |
|---|---|---|---|---|---|
| Active ingredient content after 30 days | 100% | 90.3% | 85.7% | 67.0% | 37.2% |

Tablets containing mannite or sorbite instead of lactose, and liquid paraffin instead of stearin are just as unstable.

It is known [Hungarian Patent Specification No. 171,997] that the stability of prostaglandin-containing injection preparations can be increased by the addition of alkali metal acetates to a large extent. This method, however, has not led to an increase in stability of prostaglandin-containing tablets.

DESCRIPTION OF THE INVENTION

It has now surprisingly been found that stable tablets, suitable for cervical and sublingual administration are obtained, when to the mixture to be tabletted a buffer is added, which ensures a slightly acidic (about 3 to 5) pH in the molecular liquid film on the surface of tablets, which forms due to the humidity of air. Preferred buffers include citric acid/citrate and dialkali metal hydrogen phosphate/tartaric acid systems. The tablets can further contain saccharides; sugar alcohols, e.g. lactose, mannite; optionally sweetening agents, e.g. saccharin; aromatizing agents, e.g. cyclodextrin aroma complexes, and formulation auxiliaries. By the ratio of stearic acid and alkali earth metal stearates the rate of release of the active ingredient can be controlled.

According to the invention 0.2 to 20% by weight of one or more prostaglandins are granulated with 0.4 to 40% by weight of a non-toxic buffer, which adjusts the pH of the liquid film formed on the surface of the solid phase under the influence of air humidity, to 3 to 5, 1 to 50% by weight of stearic acid, 0 to 15% by weight of an alkali earth metal stearate, 10 to 95% by weight of lactose and/or mannite, 0 to 15% by weight of a granulation aid, 1 to 30% by weight of a disintegrating agent and optionally 0.5 to 10% by weight of a flavoring and aromatizing substance, and the granulate obtained is pressed into tablets under a pressure of 500 to 2000 kp./cm$^2$. (49.03 to 196.13 MPa).

The final pressure during pressing the tablets preferably is between 800 and 1600 kp./cm$^2$. (78.45 and 156.91 MPa), since under these conditions also crystallization takes place in the tablets, and the single crystal-like, heterogeneous structure slows down the disintegration of the tablets, accordingly decreases the rate of the release of the active substance, and ensures a constant release.

In the context of the present invention the term "tablet" in a broad sense includes all compositions prepared by pressing, which contain the above-listed ingredients in the given proportions, and are prepared by employing the pressures given above. Such tablets include the conventional diskshaped, planar or spheroidal tablets and also those rod-shaped pressed preparations, which can be considered as multiplied forms of the conventional small tablets, along their longitudinal axis. This rod-shape is especially advantageous when compositions for cervical use are formulated. The cervical tablets, which are preferably 10 to 15 mm. long and 3 mm. wide, release their active ingredient content uniformly, in the full length of the cervical canal. This is advantageous for the patient and the attending physician as well, since the preparation of a series containing the desired dose from the "classical" tablets, having a lower active ingredient concentration, prior to treatment can be avoided.

In the following table the results of the X-ray diffraction analysis of a tablet prepared according to the invention and lactose, which is the major additive in the tablet are shown. The analysis was carried out with a Philips powder diffractometer, using a Ni-filtered Cu $K_\alpha$ ray, at 40 kV, 20 mA, in the range of 3° to 40° theta. The tablet tested was prepared by the process disclosed in Example 1.

TABLE

| 2 theta [°] | Relative peak amplitude [%] Tablet according to Example 1 | Lactose |
|---|---|---|
| 12.3 | 28 | — |
| 14.7 | — | 5 |
| 16.2 | — | 25 |
| 16.4 | 25 | — |
| 17.2 | 8 | — |
| 17.8 | — | 5 |
| 19.2 | 37 | — |
| 19.5 | 51 | — |
| 19.6 | — | 100 |
| 20.0 | 65 | — |
| 20.9 | 20 | — |
| 21.2 | — | 30 |
| 21.3 | 26 | — |
| 22.7 | 11 | — |
| 23.0 | — | 5 |
| 23.6 | 18 | 20 |
| 25.4 | — | 15 |
| 25.7 | 11 | — |
| 27.5 | 8 | 10 |
| 28.1 | — | 10 |
| 33.2 | 6 | — |
| 34.6 | 7 | — |
| 34.9 | 7 | — |
| 36.3 | 6 | — |
| 37.0 | 8 | — |
| 37.6 | 10 | — |

Clinical tests of 2.5 mg. $PGF_{2\alpha}$-containing cervical tablets have given the following results.

| Dilation of os uteri [mm.]: | 3–4 | 4–5 | 5–6 | 6 |
|---|---|---|---|---|
| Number of patients: | 46 | 74 | 78 | 21 |
| [%]: | 21 | 74 | 76 | 10 |
| Width of os uteri [Hegár units]: | 7–8 | 8–9 | 9–10 | 10 |
| Number of patients: | 41 | 80 | 76 | 20 |
| [%]: | 19 | 37 | 35 | 9 |
| Side effect: | pain | nausea, vomitus | other (headache) | |
| Number of patients: | 25 | 3 | 4 | |
| [%] | 11.4 | 1.4 | 1.9 | |

The os uteri was in all cases diluted in an extent, which rendered a further dilution before abortion unnecessary. In 32 cases the abortum appeared in the os uteri in 90 minutes. A control examination carried out 3 months after the treatment showed the cervical os functionally normal.

The tests were carried out as follows. Into an applicator suitable for positioning a Szontágh intrauterinal pessarium 4 to 7 tablets were placed, the applicator was introduced into the cervical canal in a depth of about 15 mm., and the tablets were pushed out of the applicator. In this way a part of the tablets could penetrate also the salpinx. The width of the cervical os was determined immediately after positioning the tablets and 60 and 90 minutes after treatment. The data obtained after 60 and 90 minutes, respectively were essentially identical.

Further details of our invention are to be found in the following examples, which are not intended to limit our invention in any way.

EXAMPLE 1

Cervical tablets of the following composition are prepared:

| | |
|---|---|
| $PGF_{2\alpha}$ | 2.5 mg. |
| lactose | 22.35 mg. |
| polyvinyl pyrrolidone | 1.40 mg. |
| sodium citrate | 1.25 mg. |
| citric acid | 1.25 mg. |
| stearic acid | 1.0 mg. |
| calcium stearate | 0.25 mg. |
| | 30.00 mg. |

The active ingredient is dissolved in a 1.6-times volume of ethanol, and the solution obtained is diluted with water to twice its volume. A homogeneous mixture of the remaining powdered solid components is granulated with this solution, the granulate is dried and re-granulated. Granulation is carried out to obtain a product, in which 20% of the granules has a particle size of less than 0.63 mm. and a volume weight of 0.5 g./cm³.

Tablets are prepared with a diameter of 3 mm., using a final pressure of 800 to 1600 kp./cm².

The strength of the tablets obtained is about 2.3 to 2.8 kp., measured by an Erweka apparatus. The tablets dissolve in distilled water, at 37° C. in 18 to 20 minutes.

To test the storability (stability), the tablets were kept at different temperatures, in air for 30 days, and their active ingredient concentration was determined. The following results were obtained:

| Temperature (°C.): | 0 | 30 | 40 | 50 | 60 |
|---|---|---|---|---|---|
| Active ingredient conc. (%): | 100 | 99.0 | 95.6 | 89.5 | 74.1 |

From the data obtained it can be calculated by the kinetic prediction method [Gyógyszerészet, 18, 81–90 (1974)] that in the cervical tablets, at a storage temperature of 20° C., in 2 years the active ingredient concentration decreases from 2.5 mg. to at most 2.47 mg., and thus the stability of the tablets is about twice the stability of conventionally prepared tablets.

EXAMPLE 2

Sublingual tablets are prepared using the following ingredients:

| | |
|---|---|
| $PGF_{2\alpha}$ | 0.2 mg. |
| lactose | 42.98 mg. |
| polyvinyl pyrrolidone | 2.33 mg. |
| sodium citrate | 0.1 mg. |
| citric acid | 0.1 mg. |
| stearic acid | 1.67 mg. |
| calcium stearate | 0.42 mg. |
| aromatizing β-cyclodextrin inclusion complex | 1.20 mg. |
| saccharin | 1.0 mg. |
| | 50.00 mg. |

$PGF_{2\alpha}$ is dissolved in 15-times amount of ethanol, the solution is diluted with water to twice of its volume, whereupon the homogenous mixture of the remaining solid components—except aroma β-cyclodextrin inclusion complex—is granulated with this solution. The granulate is dried, reduced in size to about 0.32 mm. and the aroma β-cyclodextrin inclusion complex is added. The mixture is pressed into tablets having a diameter of 5 mm., under a final pressure of 600 kp./cm². The strength of the tablets obtained is 2.5 kp., measured with an Erweka apparatus.

As an aromatizing β-cyclodextrin complex; for example, vanilline can be used. The aroma complex is only an optional ingredient in the composition. If no aromatizing complex is present, the quantity of the lactose is increased by 1.20 mg.

EXAMPLE 3

50 g. of $PGF_{2\alpha}$ are dissolved in 350 ml. of ethanol, the solution is diluted with 150 ml. of water and a previously homogenized powder mixture of 85 g. of lactose, 65 g. of mannite, 11 g. of stearic acid, 15 g. of magnesium stearate, 16.5 g. of disodium hydrogen phosphate, 8.5 g. of tartaric acid and 15 g. of polyvinyl alcohol is granulated with this mixture. The granulate is dried and regranulated. From the granulate obtained 5000 pieces of 50-mg. tablets are prepared, under a pressure of 1200 kp./cm$^2$.

EXAMPLE 4

20 g. of crystalline 15-methyl-$PGF_{2\alpha}$ are homogenized with 2300 mg. of anhydrous lactose in a powder mixer at high r.p.m. To the homogenizate previously homogenized powder mixture of 10 g. of sodium citrate, 7 g. of citric acid, 3 g. of tartaric acid, 176 g. of stearic acid, 42 g. of calcium stearate, 100 g. of saccharin, 2000 g. of anhydrous lactose and 120 g. of an aroma $\beta$-cyclodextrin inclusion complex is added. The water-content of the mixture is adjusted to 1.8 to 2.2%, whereupon 100,000 pieces of 48-mg. sublingual tablets are pressed, under a final pressure of 1000 kp./cm$^2$.

EXAMPLE 5

35 g. of $PGF_{2\alpha}$ and 15 g. of 15-methyl-$PGF_{2\alpha}$ are dissolved in 400 ml. of ethanol, the solution is is diluted with 400 ml. of water, and it is sprayed onto a previously powdered and homogenized mixture of 450 g. of lactose, 28 g. of polyvinyl pyrrolidone, 125 g. of sodium citrate, 125 mg. of citric acid and 250 g. of stearic acid. The water-content of the mixture is adjusted to 0.8 to 1.5%, whereupon cervical tablets having a diameter of 2.5 mm. are pressed, under a final pressure of 1600 kp./cm$^2$., weighing 60 mg. each.

Clinical tests on the cervical tablets prepared according to Examples 3 and 5 gave the same results as those carried out on the tablets according to Example 1.

Sublingual tablets according to Examples 2 and 4 were administered to women in labor. Labor was considerably facilitated by administration of tablets. The cervical canal became smoother, and the spontaneous retractions of the womb were increased. After labor the cervical os was contracted again in a short time, and thus the danger of infection after labor was reduced.

EXAMPLE 6

Vaginal tablets were prepared following the procedures hereinabove described, starting from the following ingredients:

| | |
|---|---|
| $PGF_{2\alpha}$ | 20.0 mg. |
| lactose | 326.5 mg. |
| polyvinyl polypyrrolidone | 123.0 mg. |
| sodium citrate | 12.0 mg. |
| citric acid | 1.0 mg. |
| magnesium stearate | 10.0 mg. |
| stearin | 5.0 mg. |
| polyvinyl pyrrolidone | 2.5 mg. |
| | 500.0 mg. per tablet |

The diameter of the tablets is 13 mm.

EXAMPLE 7

Cervical tablets are prepared starting from the following ingredients:

| | |
|---|---|
| $PGF_{2\alpha}$ | 2.5 mg. |
| lactose | 22.35 mg. |
| sodium citrate | 2.50 mg. |
| polyvinyl pyrrolidone | 1.40 mg. |
| stearin | 1.00 mg. |
| calcium stearate | 0.25 mg. |
| | 30.00 mg. per tablet |

The powdered components are homogenized, the powder mixture is granulated with an ethanolic mixture of $IGF_{2\alpha}$, the granulate is dried and after regranulation 30-mg. tablets are pressed.

We claim:

1. A stablized, prostaglandin-containing tablet with controlled rate of solubility, for local use, comprising 0.2 to 20% by weight of at least one natural or synthetic prostaglandin, 0.4 to 40% by weight of a non-toxic buffer for adjusting the pH of the liquid film formed on the surface of the solid phase due to air humidity to 3 to 5, 1 to 50% by weight of stearic acid, 0 to 15% by weight of an alkali earth metal stearate, 10 to 95% by weight of lactose and/or mannite, 0 to 15% by weight of a further granulation aid, 1 to 30% by weight of a disintegrating agent and optionally 0.5 to 10% by weight of a flavoring and aromatizing substance, tabletted under a pressure of 500 to 2000 kp./cm$^2$.

2. A process for loosening the cervical os and/or inducing labor or abortion, which comprises placing tablets as defined in claim 1 into the cervical canal or administering them sublingually.

3. A process for the preparation of stabilized, prostaglandin-containing tablets with controlled rate of solubility, for local use, which comprises granulating 0.2 to 20% by weight of at least one natural or synthetic prostaglandin, 0.4 to 40% by weight of a non-toxic buffer, which adjusts the pH of the liquid film formed on the surface of the solid phase due to air humidity, to 3 to 5, 1 to 50% by weight of stearic acid, 0 to 15% by weight of an alkali metal stearate, 10 to 95% by weight of lactose and/or mannite, 0 to 15% by weight of a further granulation aid, 1 to 30% by weight of a disintegrating agent and optionally 0.5 to 10% by weight of a flavouring and aroma substance, and tabletting the granulate obtained under a pressure of 500 to 2000 kp./cm$^2$.

4. A process as claimed in claim 3, which comprises using $PGF_{2\alpha}$ as the prostaglandin.

5. A process as claimed in claim 3, which comprises using 15-methyl-prostaglandin $F_{2\alpha}$ as the prostaglandin.

6. A process as defined in claim 3, which comprises using an alkali metal citrate/citric acid system as said buffer.

7. A process as defined in claim 3 which comprises using a dialkali metal hydrogen phosphate/tartaric acid system as said buffer.

8. A process as defined in claim 3 which comprises using magnesium or calcium stearate in the granulate.

9. A process as defined in claim 3 which comprises using an aroma $\beta$-cyclodextrin inclusion complex and saccharin as an aromatizing and flavoring substance in said granulate.

* * * * *